United States Patent [19]

Graupe et al.

[11] Patent Number: 5,081,989
[45] Date of Patent: * Jan. 21, 1992

[54] MICROPROCESSOR-CONTROLLED ENHANCED MULTIPLEXED FUNCTIONAL ELECTRICAL STIMULATOR FOR SURFACE STIMULATION IN PARALYZED PATIENTS

[75] Inventors: Daniel Graupe, Highland Park; Amihadar Arber, Skokie; Silvano A. Romeo, Franklin Park, all of Ill.

[73] Assignee: Sigmedics, Inc., Northfield, Ill.

[ * ] Notice: The portion of the term of this patent subsequent to May 14, 2008 has been disclaimed.

[21] Appl. No.: 515,163

[22] Filed: Apr. 26, 1990

Related U.S. Application Data

[63] Continuation-in-part of Ser. No. 335,197, Apr. 7, 1989, Pat. No. 5,014,705.

[51] Int. Cl.$^5$ .............................................. A61N 1/00
[52] U.S. Cl. .......................... 128/419 R; 128/423 W; 128/421
[58] Field of Search ................... 128/419 R, 421, 422, 128/420.5, 420.6, 903, 423 W

[56] References Cited

U.S. PATENT DOCUMENTS 4,724,842  2/1988  Charters ........................ 128/423 W
4,934,368  6/1990  Lynch ............................ 128/419 R

*Primary Examiner*—Francis Jaworski
*Assistant Examiner*—George Manuel
*Attorney, Agent, or Firm*—Sitrick & Sitrick

[57] ABSTRACT

In accordance with the present invention, a functional electrical stimulation system enables upper-motor-neuron paraplegic patients and certain other paralyzed or partially paralyzed patients to stand and to take steps with the support of a walker in an independent fashion so that they are in control of the stimulation and, noting that they have very little or no sensation, that they still can obtain some feedback on the state of the system. In one embodiment, a compact and safe battery-operated stimulation system is provided that is of pocket size and that allows for non-invasive save and controlled stimulation using skin surface electrodes. The system of the present invention is a stimulation system for providing upper-motor-neuron paralyzed patients with capabilities of unbraced standing and unbraced walking, which consists of a single pulse power and amplifier that outputs various trains of stimulation pulses and which is totally under microprocessor generation and control, where the microprocessor's microcomputer selectively performs multiplexing of the pulse trains and their selective alternate distribution to the various surface electrodes attached to the skin of the patient at the appropriate stimulation locations. It also controls pulse-width, pulse-frequency, pulse-amplitude and pulse-shape.

The system measures, analyzes, computes, activates and implements safety measures to protect the patient during steps, when sitting down, and in case of a malfunctioning electrode.

22 Claims, 8 Drawing Sheets

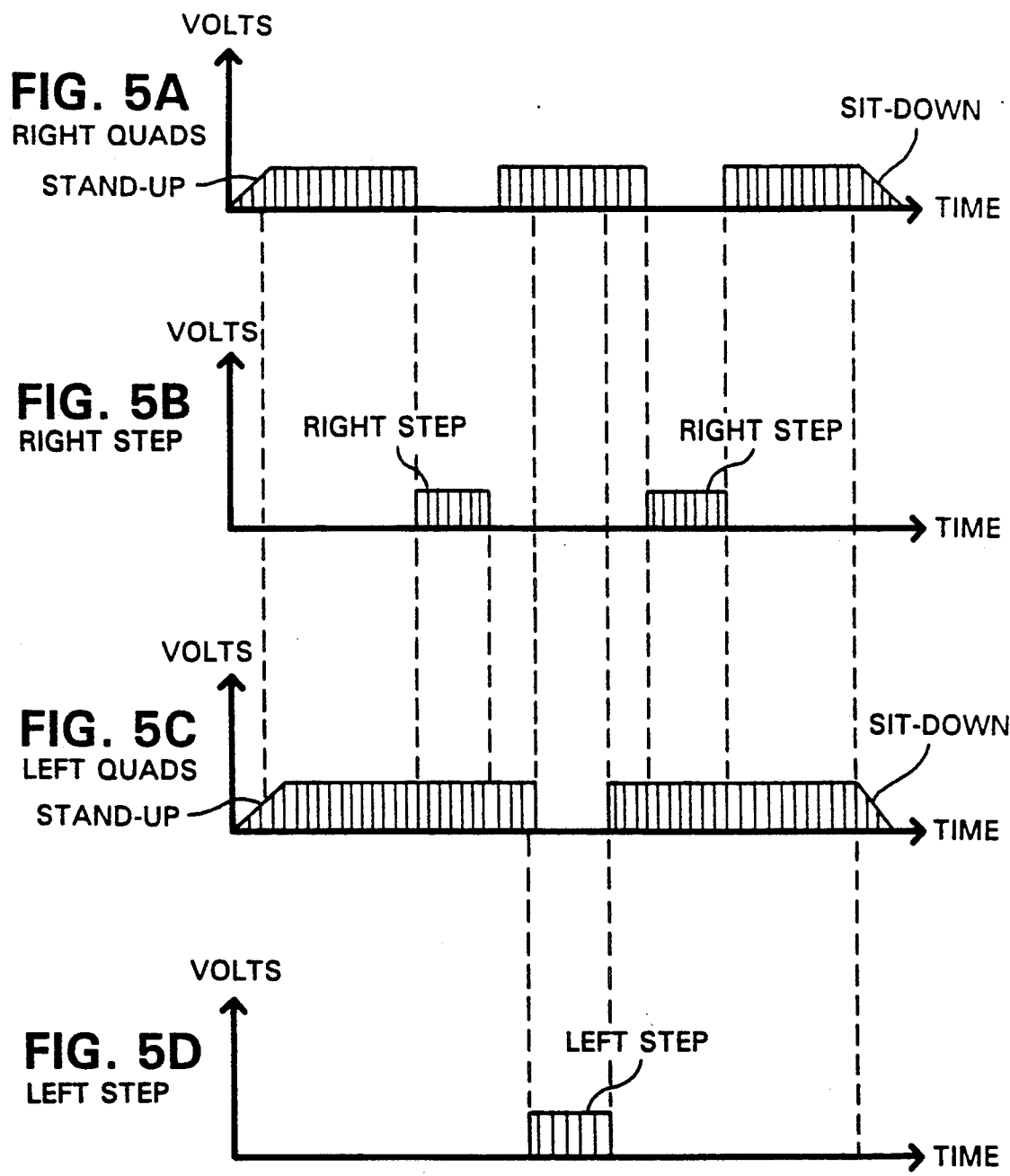

5,081,989

MICROPROCESSOR-CONTROLLED ENHANCED MULTIPLEXED FUNCTIONAL ELECTRICAL STIMULATOR FOR SURFACE STIMULATION IN PARALYZED PATIENTS

This application is a continuation-in-part of co-pending application Ser. No. 07/335,197, filed Apr. 7, 1989, now U.S. Pat. No. 5,014,705.

BACKGROUND

This invention relates to functional electrical stimulation (FES) of paraplegics and more particularly to an improved microcomputer controlled apparatus and methodology. Work on functional electrical stimulation of paraplegics is based on the discovery of the Italain physiologist Luigi Galvani in the late 18th century that a muscle will contract when in contact with an electrical charge. This has been first applied systematically to paralyzed patients by W. Liberson in 1960 (in W. Liberson et al., Arch. Phys. Med. Rehab., Vol. 42, p. 101, 1961). Since then considerable work has been devoted to that topic, as reviewed by Graupe et al. (J. Biomed Eng. Vol. 5, pp. 220–226, July 1983), by Graupe et al. (Critical Reviews in Biomedical Engineering, CRC Press, Vol. 15, pp 187–210, 1988) and in a recent text by A. Kralj and T. Bajd ("Functional Electrical Stimulation: Standing and Walking after Spinal Cord Injury", CRC Press, Boca Raton, Fla., 1989).

It was thus shown that the application of trains of pulses of adequate amplitude, pulse-width and pulse-repetition-frequency at appropriate locations above the region of certain key muscle, enables paraplegic patients with complete or near-complete upper-motor-neuron lesions to stand up and to take steps with the support of parallel bars or a walker. The merits of such standing and of the primitive walking accomplished by these steps is both psychological and physiological in the exercise provided to the patient which enhances circulation, cardiac output and movement of joints to prevent or slow down ossification and contractures (Kralj and Bajd, "Functional Electrical Stimulation: Standing and Walking after Spinal Cord Injury," CRC Press, Boca Raton, FLa., 1989, pp. 33, 68, 130–131). Furthermore, there are indications (not yet fully proven due to the limited application of FES which is presently available only in research labs and research clinics), that FES is beneficial in prevention or reduction of incidence of pressure sores and of osteoporosis (Krajl and Bajd, same as above, pp. 8, 33, 49, 69, 131 & 135) and in the reduction of severity of spasticity (Krajl and Bajd, same as above, pp. 3, 8, 37–47). FES is limited to upper-motor-neuron lesions since in that case the peripheral nerves (at the lower extremities, in our case) are intact though they cannot communicate with the central nervous system due to the spinal-cord lesion. However, since the peripheral nerves are healthy and intact, they respond to FES even after many years of paralysis without stimulation. In two patients, after 35 years of paralysis and with no stimulation over that whole time, the peripheral nerves responded to FES fully satisfactorily.

SUMMARY

In accordance with one aspect of the present invention, the present system provides non-invasive electrical stimulation for paralyzed patients with upper-motor-neuron lesions so as to provide capabilities for unbraced standing and walking. In a preferred embodiment, only a single pulse power and amplitude amplifier of stimulation pulses is utilized, in contrast to the multiple pulse amplifiers that are presently used (usually one per stimulation channel), noting that systems using multiple pulse-amplifiers require relatively heavy and cumbersome hardware, since, for patient walking purposes, a multitude of output-stimulus pulse channels (four at least) are required.

The use of a single pulse-amplifier for multiple channel stimulation is achieved in the present invention by the use of a microprocessor (microcomputer) controller system that provides output channel multiplexing and which also generates stimuli pulses and controls pulse-width, pulse-amplitude, pulse-repetition-frequency and which provides warning (preferably audible) to the patient when the system saturates. As an example, the system provides warning when muscle fatigue is such that no further increase in pulse-amplitude is possible to combat the fatigue (i.e. to recruit further muscle fibers not reached by the present electrical fields produced by the stimuli), due to reaching maximal predetermined pulse levels.

In accordance with another aspect of the present invention, the system provides the combination of multiplexing and of complete microprocessor (microcomputer) control including microprocessor controlled warning and microprocessor-controlled provisions of fail-safe features. The warning aspect is of major importance since the patient, being paralyzed, cannot feel muscle fatigue. The warning is determined responsive to computerized sensing of the appropriate control input levels, which the patient sends, such as through activating manual finger-switches attached to the walker, as control inputs to the microprocessor controller, to increase the level of the stimuli when he senses, via pressure in his arms (which hold the support of the walker,) that he needs higher such levels. Alternatively, the control inputs can be automatically generated from feedback signals derived from the patient (such as via sensing electrodes).

The significance of the provision of fail-safe features for situations where certain major system failures occur is very important, since the system is designated for use by paralyzed persons who have no sensation at their lower extremities. These persons depend on these stimulator's safety features, and the above failures without fail-safe features, may cause them to fall, noting that it is of utmost importance to prevent falls.

In accordance with another aspect of the present invention, directed to the safety feature of preventing falls, the system provides an increased level of stimulus to the standing remaining quad for the duration of a step by the other leg during each step, by a predetermined increase level value. This provides a safety mechanism to prevent possible falls of a patient while taking a step. When taking a step, all of the patient's weight is on the leg not stepping, the stepping leg being in the air (being moved to produce a step). The computing portion of the system determines both when to take the step, and at the appropriate time of taking the step, increases the stimulus to the remaining quad by between ten and twenty percent above the ten steady state level In accordance with another aspect of the present invention, solid state cascaded voltage-doublers are used, instead of the heavier pulse-transformers, for the purpose of stimuli pulse-generation. Another innovative aspect of the present invention is the employment of a telemetry link between the walker-mounted patientoperated switches and the stimulator itself, to avoid the employment of wires between walker and the usually patient-borne stimulator.

In accordance with yet another aspect of this invention, in order to avoid high voltage at channel outputs under no-load conditions, the output of the pulse-amplifier circuit may be connected to a voltage-sensitive load, such as a fast ZNR transient surge resistor (e.g. a zinc-oxide nonlinear resistor device) in series with an appropriate load resistor, such that the output channels to the stimulation electrodes, that are attached to the patient, will be loaded by a resistance of no more than a few thousand ohms if the output of the pulse-generator circuit (e.g. pulse-transformer) exceeds some predetermined voltage (such as in the range of 50 to 130 volts).

In accordance with another aspect of this invention, opto-isolators are coupled from the output of the channel outputs and to the electrodes, so as to provide isolation of the various output channels, so as to avoid back current from feeding back into the microprocessor and other circuitry, and so as to isolate the various output channels to prevent cross-talk.

In accordance with another aspect of this invention, any command to activate a "sit-down" mode (in order to stop stimulation when the patient wishes to sit-down), may be overridden by pressing of any command switch, to avoid that the patient may fall if inadvertently activating the "sit-down" command. Also, when the "sit-down" command switch is pressed, the sit-down function which under the present invention implies gradual cessation of stimulation to the patient's quadriceps muscles, will be delayed under an aspect of this invention in its execution of this gradual reduction of stimuli to zero by a predetermined number of seconds, (e.g. 5 to 12 seconds). Furthermore, under again another aspect of this invention, the activation of the sit-down command will immediately give the patient a warning signal which may be flashing light on the walker to indicate the patient that the "sit-down" function has been initiated.

Additional safety features are also associated with the "sit-down" mode. First, since the computer is determining when to take steps, it can time events precisely. As one additional safety feature, when going to a sit-down mode, the system increases stimulus level to both the right and left quadriceps muscles via the electrodes for attachment thereto, thus giving extra support to the quads for sitting, since the person may already be fatigued at this point where they are ready to sit-down. The increase in level is in the range of ten to 20%.

In accordance with another aspect of the present invention, the system measures it's own output current between the multiplexer and the electrodes (or alternatively it can measure the voltage drop over a fixed impedance at that location) and couples the measurement value back to it's input for determination of whether the output current (or voltage) drop is below a predefined threshold. The predefined threshold, in a preferred embodiment, is approximately 50% of the lowest output level to any electrode. Alternatively, by trial and error, other thresholds can be chosen. If there is a drop below this predefined threshold, this implies that enough current is not being output to some channel (or channels), i.e. such as an electrode is loose or disconnected. The computing unit of the apparatus then provides an audible sound alarm and/or visual alarm for the user/patient, and disallows any step, but maintains the patient in a standing mode (at least on one leg since during a step one leg is in the air). If the other leg happens to be the one disconnected (the one being stood on is the one where the electrode disconnects), then the patient will fall, except as self-supported by his/her arms on a walker unit.

In describing use of this system for upper-motor-neuron paraplegics, noting that this invention is concerned with standing and walking by such paraplegics implies limitation of the system to patients whose spinal cord lesion is virtually at the thoracic T12 level or higher (approximately above the belt level). The functions and features as discussed above and their combination in the manners discussed above are essential and unique for applications to standing and walking by paralyzed patients. This constitutes a major and essential difference from any stimulator for pain relief or for exercise of muscle where no walking is intended to be stimulated and controlled.

BRIEF DESCRIPTION OF THE DRAWINGS

The present invention may be better understood by reference to the written specification in conjunction with the drawings, wherein:

FIG. 5A-D provide voltage vs. time waveforms illustrating the envelope of pulses as distributed to four channels during FES activated walking;

DETAILED DESCRIPTION OF THE DRAWINGS

Figure 1:
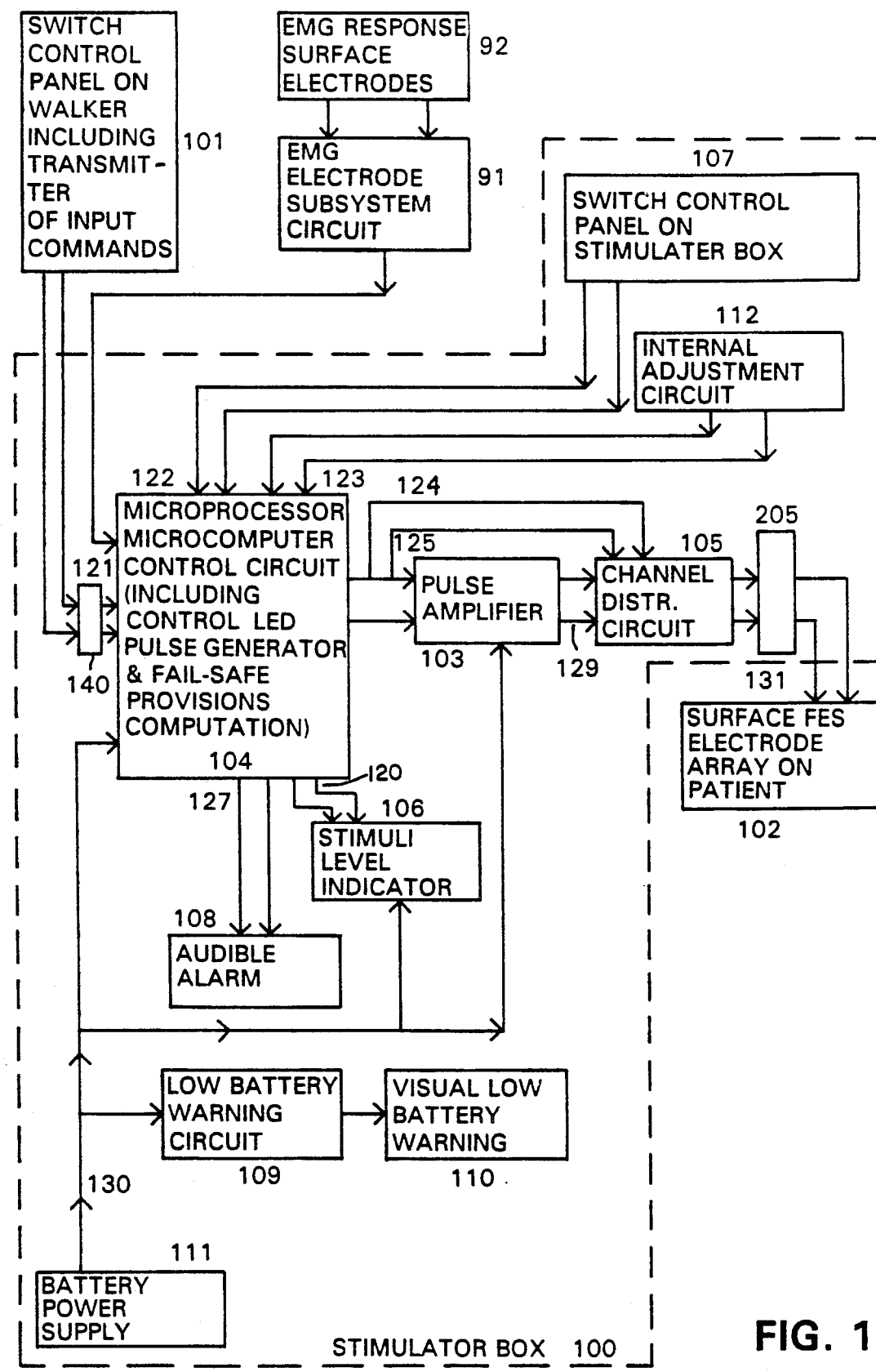
FIG. 1 is an electronic schematic block diagram of one embodiment of an FES Stimulation System in accordance with the present invention.

The FES stimulation device under this invention is a system as in FIG. 1, that comprises of an FES stimulation box 100 that is battery-operated 111, using AA or AAA 1.5 volt batteries or similar batteries, and which includes a stimuli pulse-generator 103, a microprocessor-control circuit 104 and related interface and which has a control panel 107 of pressure switches on its cover.

The same stimulator box 100 also houses the telemetry (ultrasound or radio frequency, or infra-red) receiver in realizations of the invention where telemetry is employed. Alternatively, connector interface circuitry can be provided for non-telemetry applications. It may also house the audible warning element 108, and may house a low-battery voltage indicator 109 and/or a low-battery visual 110 or audible warning 108 and a display of stimuli levels that is activated to show the level of a given channel when the appropriate control switch is activated by the user. The stimulation box 100 is connected on its input side 121 to walker-mounted hand (finger) switches (switching unit) 101 and on its output side 124 to the stimulation surface electrodes 102 attached to the patient. The complete system with a patient is shown in FIG. 2A.

Figure 2A:
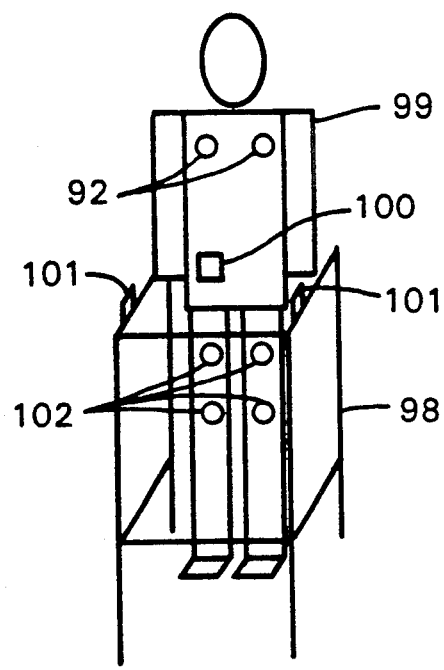
FIG. 2A shows the complete system with walker, patient and FES stimulator box.

Referring to FIG. 2A, paraplegic user 99 is shown supporting himself with his arms, and by use of the present FES system, with a walker 98 having finger switches control unit 101 mounted thereto, and the FES stimulator box 100 affixed to his belt.

Figure 2C:
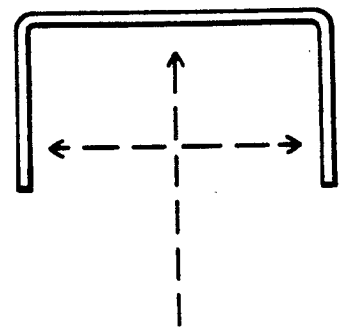
FIG. 2C shows a top view of the walker of FIGS. 2A-B.
Figure 2B:
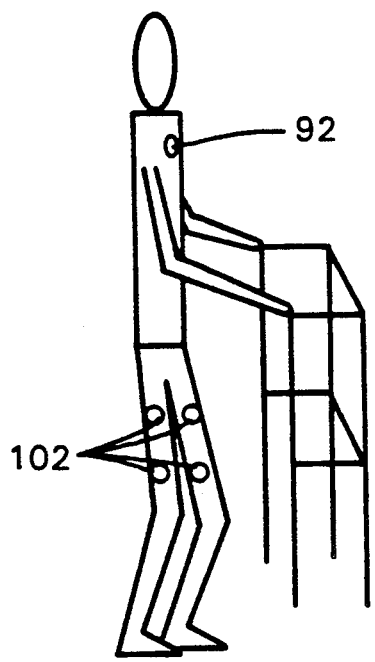
FIG. 2B shows a side view of FIG. 2A

FIG. 2B illustrates a side view of FIG. 2A

Figure 2D:
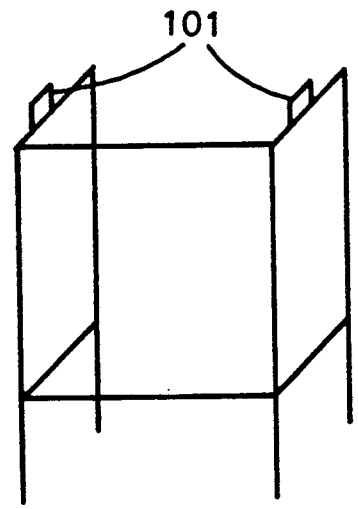
FIG. 2D shows a perspective view of the walker of FIGS. 2A-C.

FIG. 2C illustrates a top view of the walker 98, while FIG. 2D provides a perspective view of the walker 98 and finger switches control unit 101. The walker 98 is preferably constructed of aluminum pipe, of from $\frac{1}{2}''$ to $1\frac{1}{2}''$ diameter, ergonomically determined, but typically $\frac{1}{2}''$ or $\frac{3}{4}''$.

Figure 3:
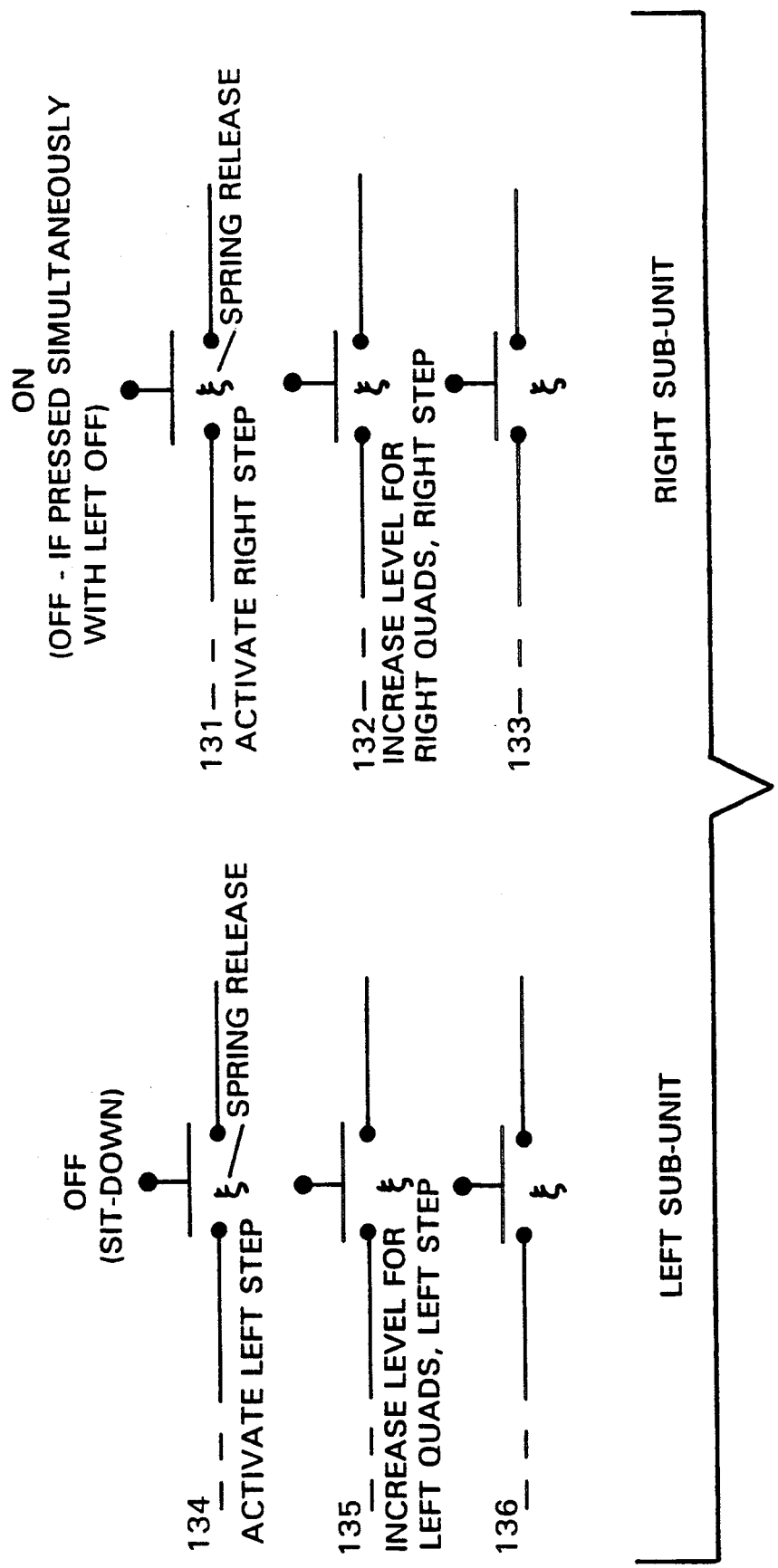
FIG. 3 illustrates one embodiment of the walker mounted switch control unit.

The switching unit 101 that is mounted on the handles of the walker 98 as illustrated in FIG. 2A, is divided into two sub-units, interconnected by wire, one on the right hand side hand-bar and one on the left-hand side handbar. The walker should preferably be a reciprocating walker, using aluminum tubing of approximately 1 inch diameter, As illustrated in FIG. 3, the right hand-side walker-mounted switching sub-unit consists of an "on/off" switch 131 for stand-up and sit-down, and of a switch 132 for activating a right step and of a switch 133 for increasing the stimulation level for both the stimulus to the right region of the quadriceps muscles (for strengthening right quadriceps muscle contractions in standing) and for the stimulus to the right peroneal nerve (for the right step), and where a short duration pressing of that switch increases the stimuli level to the quadriceps and a substantially longer such duration increases it for the right step. The left hand-side switching sub-unit includes a "sit-down" switch 134, such that the sit-down function is activated only when both the left "on/off" switch 131 and the right "off", (namely "sit down") switch 134 are simultaneously pressed, whereas standing requires pressing the right "on/off" switch 131 alone, and where one must start pressing the left "off" switch 134 before pressing the right "on/off" switch 131 and continue pressing it until after releasing the right switch 131. The left hand-side sub-unit also includes a left step switch 135 and a level increase switch 136 that again serves to both increase level of left quadriceps and of left step stimuli. Thus, there are 3 switches on each sub unit as illustrated in FIG. 3.

As illustrated in FIGS. 1-3, the switching unit 101 is connected for use with an ultrasound transmitter which via a coding circuit, both mounted on the walker, transmit the appropriate codes to the stimulator box. The codes as illustrated herein are:
(i) stand-up: press switch 131.
(ii) right step: press 132.
(iii) left step: press 135.

(iv) sit-down: press 131 and 134 simultaneously.
(v) increase stimulation to right quads (quadriceps): press 133 (short duration).
(vi) increase stimulation to left quads (quadriceps): press 136 (short duration).
(vii) increase stimulation for right step: press 133 (long duration).
(viii) increase stimulation for left step: press 136 (long duration).

This ultra-sound communication link coding circuit and transmitter, together with the appropriate receiver 140 mounted in the stimulation box 100 constitute the communications link of 121 of FIG. 1. The receiver 140 couples the received coded signal for input to the microprocessor circuit 104 where this input is decoded to determine which command is being sent from the input commands (i) to (viii) above. In an alternate embodiment, a wire link substitutes this coded ultrasound link as link 121 above. Switch 131 can be omitted in some realizations or could serve only for stand-up purposes. In these cases, sit-down is activated by a long duration activation of switch 134 alone, which could be located at the right or left sub-unit with the "stand-up" switch, if employed, being located at the opposite sub-unit.

In addition, in either realization, inputs (i) to (viii) can alternatively be inputted from the stimulator-mounted switching control panel 107 where, additionally, four further inputs can be generated. These inputs are as follows:
(ix) decrease stimulation to right quads
(x) decrease stimulation to left quads
(xi) decrease stimulation to right step
(xii) decrease stimulation to left step.

However, on this panel 107 each function (i) to (xii) may have its own switch. In a realization where the region of the gluteus maximus muscles are stimulated, then any of the above functions relating to a step should be considered as functions relating to the gluteus maximus of the same side (right or left), since it is considered that persons with a relatively unstable trunk who require stimulation of the gluteus maximus are not supposed to walk with the present system. In cases of minor trunk instability, a corsette may be worn by the patient, and walking may be executed without stimulating the gluteus maximus if approved by a medical practitioner.

The microprocessor control circuit of 104 has further inputs 123 via internal adjustment circuit 112 which includes a set of pins where applied voltages are input as (4) commands to adjust pulse rate, pulse duration (width), maximal stimuli levels, and can additionally be used to adjust duration of ramp-like envelopes of stimuli amplitudes that are employed at the initialization of stand-up and/or at the end of sit-down, these ramps being a gradual initial-increase/final-decrease of stimuli amplitudes, to avoid a too sudden start/cessation of contraction in stand-up/sit-down. For stand-up, a certain overshoot at the end of the ramps is possible, to provide contraction force for standing-up that is above the force required otherwise for standing, noting the energy required to stand-up from a sitting position.

The microprocessor 104 generates pulse trains and controls at its output 124 the pulse characteristics according to the inputs from 112 and from the switch-inputted functions concerned with stimuli level, which may either modify pulse duration or pulse amplitude. All these are outputted through 125 to the pulse and amplitude amplifier 103 whose output is multiplexed in response to the control as determined by microprocessor 104, and which serves to provide stimuli for all functions (stand, right step, left step). The pulse amplifier 103 is controlled responsive to the microprocessor via link 126 to output these pulses through the distribution interface circuit 105 as determined by the processor 104 according to the input switches of 101 or of 107. The circuit 105 thus couples the stimuli to the various skin surface electrodes (2) that are attached with tape to the skin at the appropriate stimulation locations as discussed above. Note that components 103, 104, 105, 107 and 117 are all mounted on the stimulator box 100.

In accordance with another aspect of this invention, opto-isolators are coupled from the output of the channel outputs and to the electrodes, so as to provide isolation of the various output channels, so as to avoid back current from feeding back into the microprocessor and other circuitry, and so as to isolate the various output channels to prevent cross-talk.

Opto-isolators as available from many of the commercial manufacturers of opto-isolators can be utilized, including those from Texas Instruments, Hewlett-Packard, and many, many others.

Figure 6:
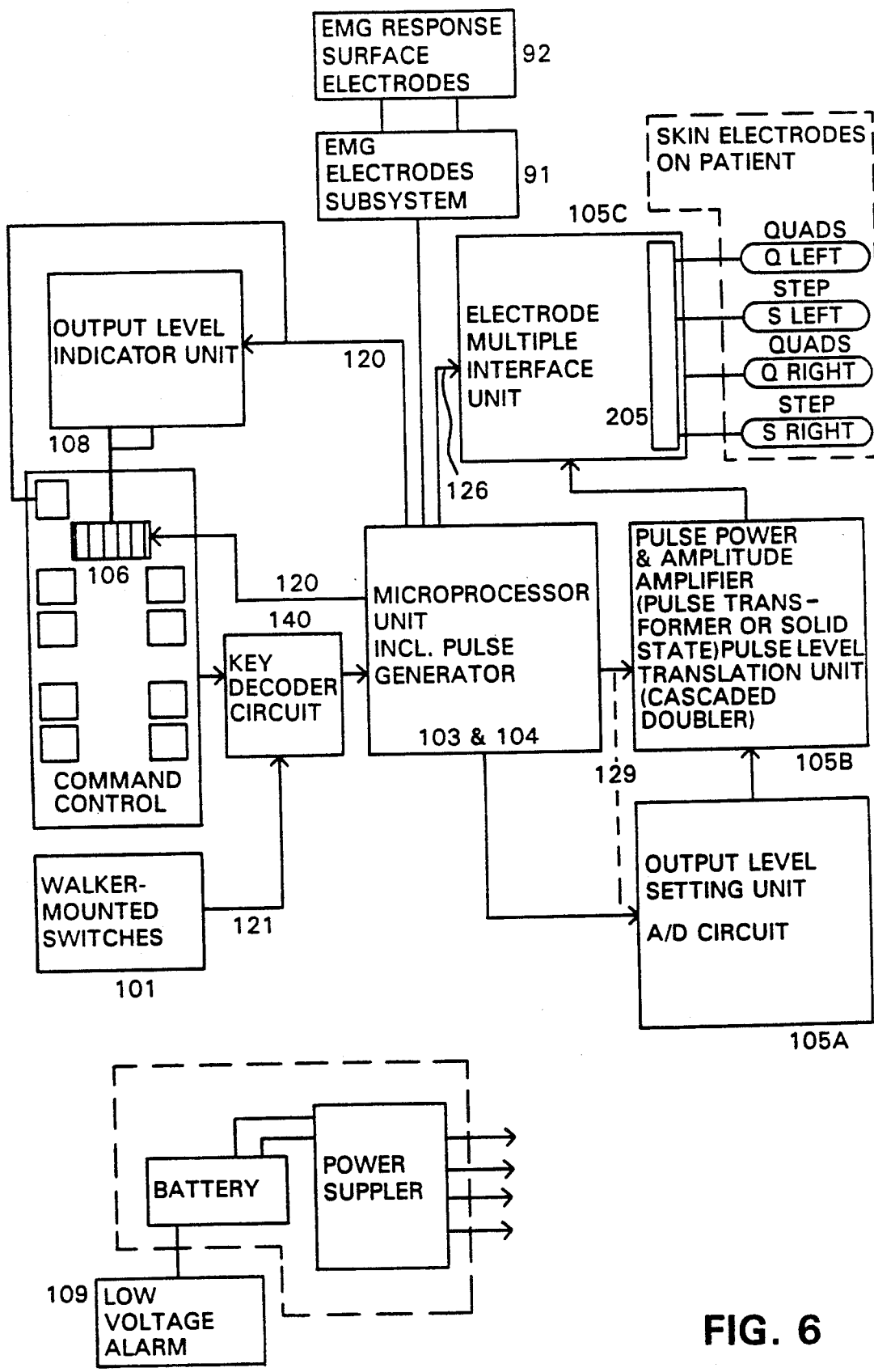
FIG. 6 illustrates an electrical block diagram for a specific alternate embodiment of a FES stimulator box.

Opto-isolators 205 are illustrated in both FIGS. 1 and 6. The optoisolators 205 are shown in dashed form in both FIGS. 1 and 6, since they may optionally be included or not included depending upon design criteria. In the preferred embodiment, the opto-isolators 205 are included, having inputs coupled from the channel distribution and multiplexing circuitry 105, and optically isolating, amplifying and coupling to the surface electrode array 102, being adapted for coupling to connectors which are coupled to cables coupled to the electrodes. Similarly, for FIG. 6, the opto-isolators 205 are shown as coupling between the electrode multiple interface unit 105C outputs and providing opto-isolation to and from the skin electrodes on the patient.

The stimuli levels are computed by counting the number of times the appropriate switches are pressed, so that each time an appropriate switch is pressed, the stimuli level at the corresponding channel is increased by a predetermined increment.

Figure 4:
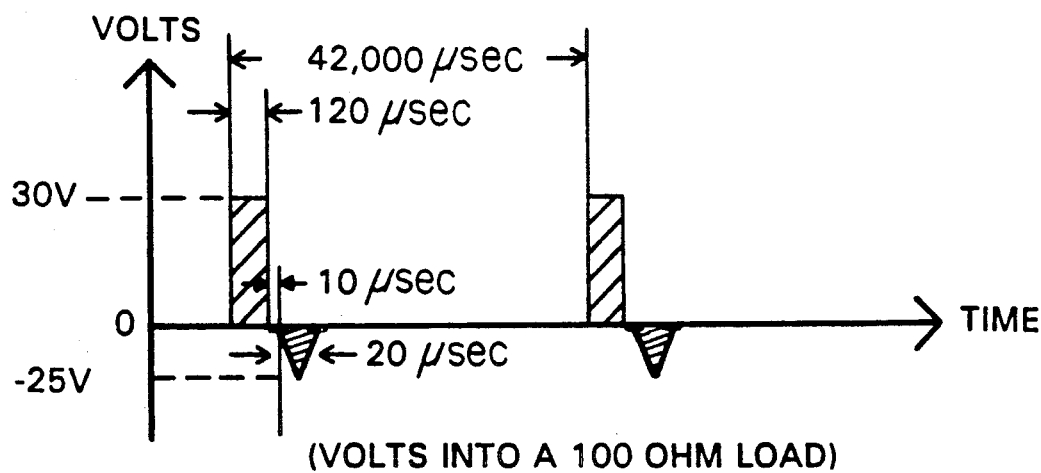
FIG. 4 illustrates the voltage pulse waveform for a typical FES system pulse output.
Figure 2E:
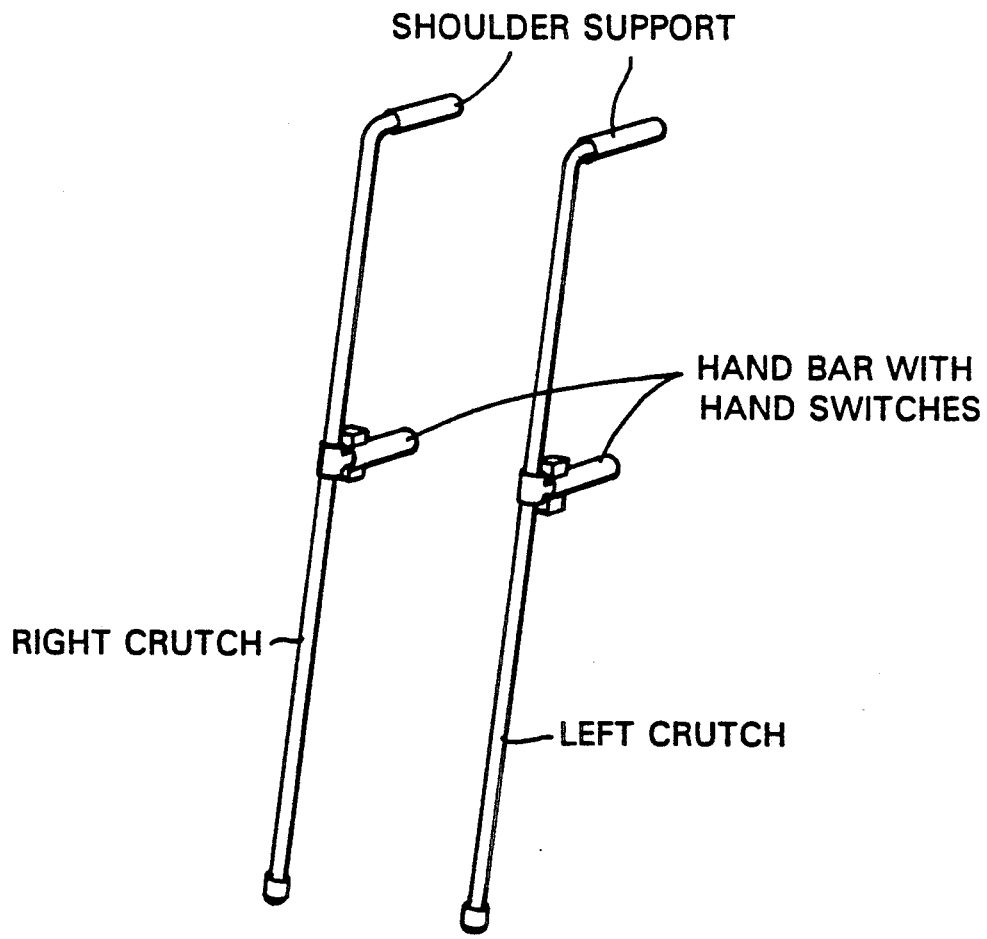

The pulse amplifier 103 can consist of a single pulse transformer or, alternatively, of a single solid state cascade of voltage doublers to output a train of pulses which may all be positive or all negative, or may have a positive component followed immediately by a negative component (or vice versa) as illustrated in FIG. 4. When quads and steps are stimulated then the pulse-rate is set by microprocessor 104 at approximately 48 pulses per second which is multiplexed at the pulse amplifier's output responsive to microprocessor 104 into 2 channels, each having a rate of 24 pulses per second. If the gluteus maximus and the quads are stimulated, then no step is activated, and the pulse rate is 96 pulses per second divided into 4 channels each having a rate of 24 pulses per second responsive to the microprocessor 104.

The distribution of the stimuli as determined by microprocessor 104 is shown in FIGS. 5A-D, showing the envelopes of stimuli pulse trains for stand and sit-down functions as applied to Right Quads (FIG. 5A) and Left Quads (FIG. 5C), and to the right and left peroneal nerves for activating Right Step (FIG. 5B) and Left Step (FIG. 5D).

In addition, microprocessor circuit 104 computes the actual stimulus level per a given function and outputs via 128 to display circuit 106. Display circuit 106 can be an LED light-bar display, or alternatively, a numerical read-out display. The display can be mounted on the stimulator box 100.

The microprocessor 104 also determines when the quads' stimulus level at any one of the two quads reaches a level close to the maximal level, as determined by 104 responsive to the inputs via 112, and then activates an audible alarm 108 to warn the patient that he cannot increase level any further. This aspect is important since the patient has no sensation at the quads and cannot determine degree of fatigue at the stimulated muscle. When walking with the FES system of the present invention, the patients arms carry only 2% to 5% of his body weight according to measurements, whereas his stimulated leg muscles carry 95% to 98%. Whenever the patient feels that his arms which support him on the walker carry increased weight, he will tend to increase quads stimuli levels at the appropriate arm side. However, when he reaches the maximum level he must be given time to sit down (possibly, to go to a chair). Hence, the alarm of 108 is to be activated in sufficient time before that complete fatigue level is reached, this level being also adjustable by processor 104 responsive to inputs at 112. The audible alarm can be mounted on the stimulator box 100.

The microprocessor circuit 104 also computes fail-safe provisions to: (i) guarantee that a step can be taken only at one leg at a time; (ii) guarantees that, if no input is received from the walker mounted switches 101 or from the panel switches 107 on the stimulator box 100, concerning commands to one leg or to both, then the patient will always be or remain in the "stand" (both quads "on") mode, to guarantee that with a failure in link 121 or 122, be it an acoustic, IR, radio frequency or wire link or transmitter or receiver failure, that the patient will remain standing and will not fall (and, of course, he still has the walker support); (iii) guarantees that after every step the system automatically returns to the "stand" mode (of both quads being stimulated), and in certain realizations the microprocessor 104 also computes a fail-safe provision that a step is limited in time so that even if a step switch is stuck in the "step" mode, then after a predetermined reasonable time (of the order of a second) the concerned leg is returned to "stand" (quads) mode by an appropriate microprocessor-controlled decision and channel switching. In certain realizations the latter situation also provides for an appropriate warning signal, audible or visible or both, to alert the patient to that faulty situation.

Additional safety features are also associated with the "sit-down" mode. First, since the computer is determining when to take steps, it can time events precisely. As one additional safety feature, when going to a sit-down mode, the system increases stimulus level to both the right and left quadriceps muscles via the electrodes for attachment thereto, thus giving extra support to the quads for sitting, since the person may already be fatigued at this point where they are ready to sit-down. The increase in level is in the range of ten to twenty percent (10%-20%).

Figure 7A:
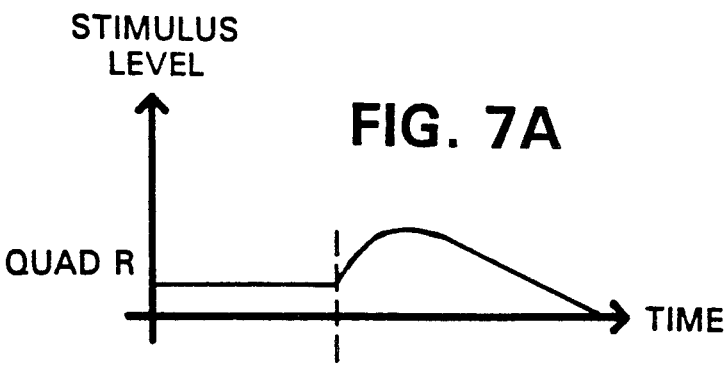
FIG. 7A shows the stimulus level plotted vertically versus time plotted horizontally for the right quadriceps muscle.
Figure 7B:
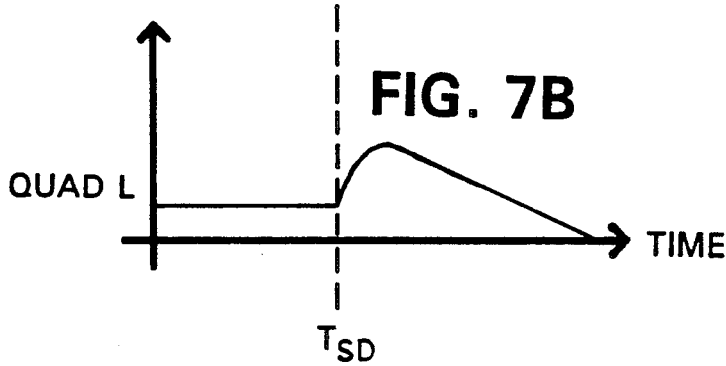
FIG. 7B illustrates the stimulus level versus time for the left quadriceps.

Referring to FIGS. 7A-B, FIG. 7A shows the stimulus level plotted vertically versus time plotted horizontally for the right quadriceps muscle, and FIG. 7B illustrates the stimulus level versus time for the left quadriceps muscle. Note that at the time indicated, $T_{SD}$ indicating the time of the sit-down command from the standing position as received and recognized by the computer, that the stimulus levels to both the right and left quadriceps muscles are increased, by between ten to twenty percent preferably, for a short time duration (on the order of seconds) prior to decreasing the stimulus level by ramping the level of the stimulus signals to the right and left quadriceps to the zero level of full sitting.

In accordance with another aspect of the present invention, directed to the safety feature of preventing falls, the system provides an increased level of stimulus to the standing remaining quad for the duration of a step by the other leg during each step, by a predetermined increase level value. This provides a safety mechanism to prevent possible falls of a patient while taking a step. When taking a step, all of the patient's weight is on the leg not stepping, the stepping leg being in the air (being moved to produce a step). The computing portion of the system determines both when to take the step, and at the appropriate time of taking the step, increases the stimulus to the remaining quad by between ten and twenty percent above the then steady state level.

Figure 8A:
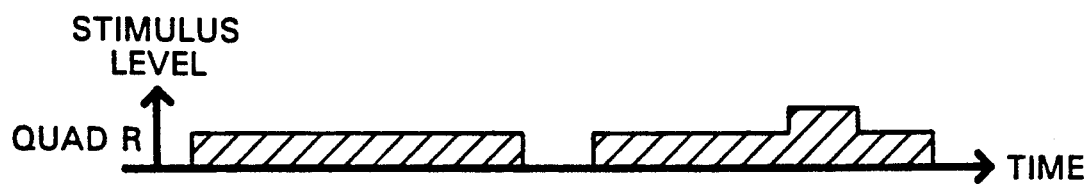
FIGS. 8A and 8B illustrate stimulus level versus time waveforms for the right quadriceps (Fib. 8A) and left quadriceps (Fib. 8B)
Figure 8B:
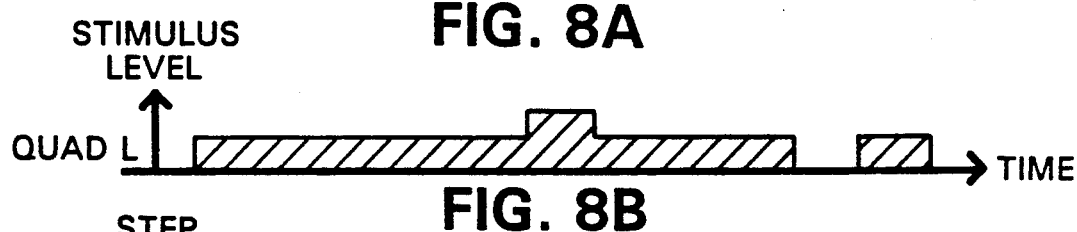
Figure 8C:
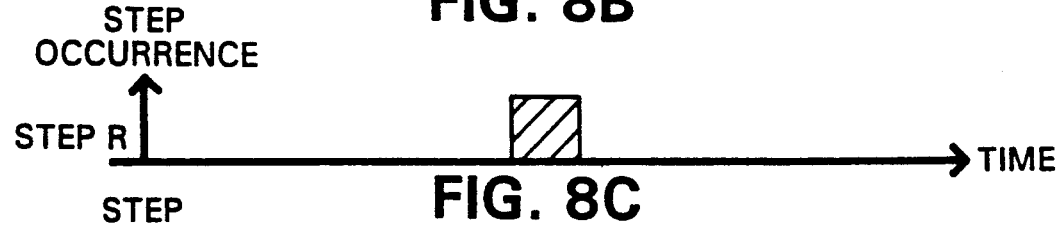
FIGS. 8C and 8D illustrate step occurrence versus time waveforms for step right (FIG. 8C) and step left (FIG. 8D); and, FIG. 9 is an electrical schematic block diagram illustrating the output level detect safety subsystem of the present invention.
Figure 8D:
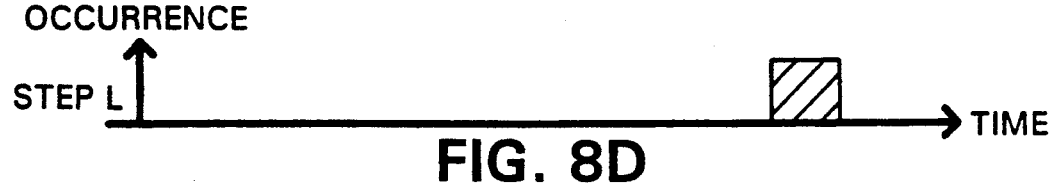
Figure 9:
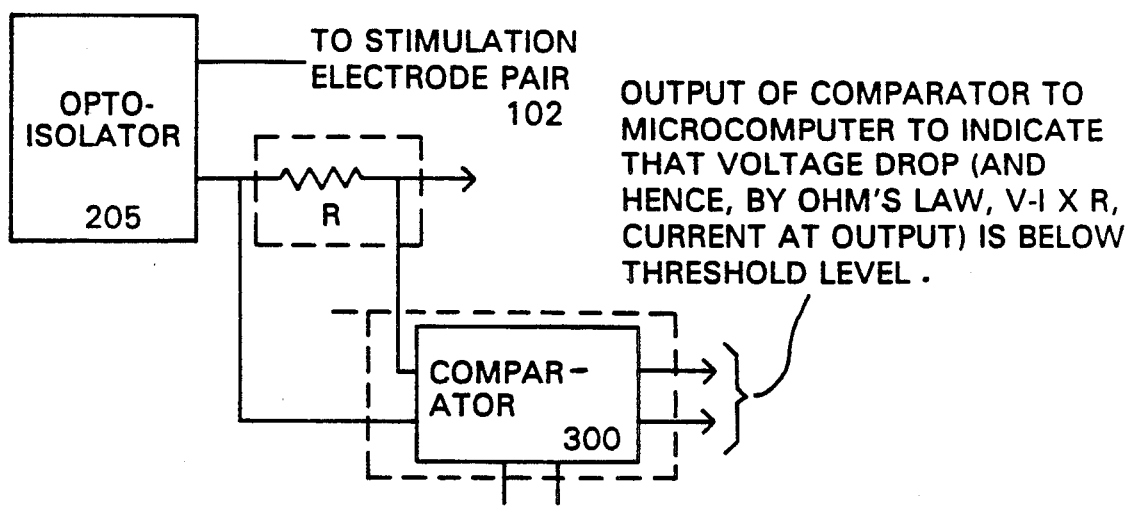

Referring to FIGS. 8A-D, FIGS. 8A and 8B illustrate stimulus level versus time waveforms for the right quadriceps (FIG. 8A) and left quadriceps (FIG. 8B). FIGS. 8C and 8D illustrate step occurrence versus time waveforms for step right (FIG. 8C) and step left (FIG. 8D). Each of FIGS. 8A-8D is plotted against the same time axis in the horizontal direction. As illustrated in FIGS. 8A-C, when step right occurs as indicated by the positive pulse on FIG. 8C, the stimulus level to the right quadriceps (FIG. 8A) is turned off during leg movement to produce the step, while at that same time, the stimulus level to the left quadriceps is incremented as illustrated on FIG. 8B, approximately 15% over the steady state level. (An increase within the range of approximately 10 to 20% is acceptable). Thus, the stimulus level to the left quadriceps is increased temporarily during the step occurrence of the right step, corresponding to the turning off of the stimulus to the right quadriceps. Similarly, referring to FIGS. 8A, 8B and 8D, at the step occurrence of step left, the positive pulse in FIG. 8D, the stimulus to the left quadriceps, FIG. 8B, is turned off, while the stimulus level to the right quadriceps, FIG. 8A, is increased by the predefined value to increase the level of stimulus to the standing leg, the right leg, during the left step. To provide extra smooth landing of a given leg after a step has been taken with that leg, it may be advisable not to stimulate the quadriceps of that leg with a sharp instantaneous voltage rise, but to provide a voltage ramp rise-time of the stimuli to these quadriceps after each step Referring to FIG. 9, in accordance with another aspect of the present invention, the system measures it's own output current such as between the opto-isolator 205 (or multiplexer means 105) and the electrodes 102 (or alternatively it can measure the voltage drop over a fixed impedance R at that location), and couples the measurement value back to it's input for determination of whether the output current (or voltage) drop is below a predefined threshold. As illustrated in FIG. 9, the output current to one electrode is determined by measuring the voltage drop ($V_D$) across a fixed impedance R. The voltage $V_D$ is compared to a predefined threshold level $V_T$ (illustrated as being variable for different preset predefined levels) by a comparator 300. The output of the comparator 300 is coupled to an input of the system's microprocessor 104. The predefined threshold, in a preferred embodiment, is approximately 50% of the lowest output level to any electrode. Alternatively, by trial and error, other thresholds can be chosen. If there is a drop below this predefined threshold, this implies that enough current is not being output to some channel (or channels), i.e. such as an electrode is loose or disconnected. The computing unit 104 of the apparatus then provides for an audible sound alarm and/or visual alarm for the user/patient, and disallows any step, but maintains the patient in a standing mode (at least on one leg since during a step one leg is in the air, preferably increasing the stimulation level to the remaining electrode). This stimulation level can be increased by increasing either the peak voltage, pulse frequency, pulse width, or a combination of these. In addition, it has been shown in the literature (of Kralj and Bajd book, page 127, FIG. 3) that by increasing pulse width and/or pulse frequency during a "TAKE STEP" mode, one achieves a higher step (a larger angle of hip joint flexion). Whereas the figure of p. 127 related to the CUTANEOUS FEMORIS nerve, our experience over many tests with patients indicates similar increases of step height (namely, of hip flexion angle) also when a peroneal nerve is being stimulated. If the other leg happens to be the one disconnected (the one being stood on is the one where the electrode disconnects), then the patient could fall, except as self-supported by his/her arms on a walker unit.

To avoid excessively high voltages at the output of the pulse-amplifier circuit 103, that output may also be connected, in parallel, to a ZNR type voltage sensitive load. This load presents to that output a load of no more than a few thousand ohms, if the voltage at that output reaches a certain predetermined value of between 50 and 130V, and which otherwise presents an additional open circuit.

A battery supply 111, as illustrated, consists of 8 AAA 1.5 VDC batteries, which supplies power to all the circuits of the stimulator box 100 via 130. The battery supply is also coupled to activate a low-battery voltage warning via circuit 109 to provide the audible warning 108 and also a visual flashing warning light 110. The "low-battery" warning sound is programmed by the processor 104 to differ from the sound of the stimulus-level-saturation alarm discussed above.

FIG. 6 illustrates a specific embodiment of the stimulator box 100 of FIG. 1, for a wired link 121, with corresponding numerals indicating like elements. Specific electronic device designations are illustrated in FIG. 6, such as the Hitachi HD63701 processor, 104.

While there have been described herein various illustrated embodiments, it will be understood by those skilled in the art that various other embodiments emanate from those disclosed. This description is illustrative and not limiting, and the true scope of this invention is as set forth in the appended claims

What is claimed is:

1. An electrical stimulation system adapted for coupling to a patient, said system comprising:
   a plurality of electrodes adapted for coupling to locations at the right and left side of a lower part of the body of a patient,
   pulse generator means for selectively providing pulse generator means outputs comprising trains of pulses having selectively variable duration and pulse repetition frequency responsive to a control signal;
   memory for storing operational instructions and data;
   control means for selectively outputting said control signal responsive to said memory and to input commands;

pulse amplifier means for selectively amplifying pulse amplitude and power responsive to said control means and said pulse generator means;

multiplexer means for providing multiplexer means outputs responsive to selectively multiplexing outputs of said pulse amplifier means and alternatively coupling said multiplexer means output between selected ones of said electrodes responsive to said control means; and, opto-isolator means, for coupling between said multiplexer means outputs and said electrodes, for buffering and optically and electrically isolating said outputs coupling to said electrodes and said electrical stimulation system.

2. An electrical stimulation system adapted for coupling to a patient, said system comprising:

a plurality of electrodes adapted for coupling to locations at the right and left side of a lower part of the body of a patient, pulse generator means for selectively providing pulse generator means outputs comprising trains of pulses having selectively variable duration and pulse repetition frequency responsive to a control signal;

memory for storing operational instructions and data;

control means for selectively outputting said control signal responsive to said memory and to input commands;

pulse amplifier means for selectively amplifying pulse amplitude and power responsive to said control means and said pulse generator means;

input command means for providing mode input command signals, wherein said control means selectively provides one of a plurality of modes responsive to said input command means; and, multiplexer means for providing multiplexer means outputs responsive to selectively multiplexing outputs of said pulse amplifier means and alternatively coupling said multiplexer means output between selected ones of said electrodes responsive to said control means;

wherein said control means switches modes of operation responsive to said input command means to provide a stand mode, a take left step mode, a take right step mode, and a sit down mode;

wherein said electrodes are wired in pairs as channels, one adapted to contact to the right quadriceps muscle, one adapted to contact to the left quadriceps muscle, and one adapted to contact to the area of right and left peroneal nerves;

wherein during the "take left step" mode the pulse outputs are selectively outputted to the right quadriceps channel and left peroneal channel, while at the same time no stimulus is outputted to the left quadriceps muscle and to the right peroneal nerve; said output to the right quadriceps channel being increased by a predefined amount during the time that no stimulus is being output to the left quadriceps channel.

3. The system as in claim 2 wherein said predefined amount is on the order of 10–20% above the immediately preceding output.

4. The system as in claim 3 wherein said predefined amount is 15%.

5. An electrical stimulation system adapted for coupling to a patient, said system comprising:

a plurality of electrodes adapted for coupling to locations at the right and left side of a lower part of the body of a patient, pulse generator means for selectively providing pulse generator means outputs comprising trains of pulses having selectively variable duration and pulse repetition frequency responsive to a control signal;

memory for storing operational instructions and data;

control means for selectively outputting said control signal responsive to said memory and to input commands;

pulse amplifier means for selectively amplifying pulse amplitude and power responsive to said control means and said pulse generator means;

input command means for providing mode input command signals, wherein said control means selectively provides one of a plurality of modes responsive to said input command means; and, multiplexer means for providing multiplexer means outputs responsive to selectively multiplexing outputs of said pulse amplifier means and alternatively coupling said multiplexer means output between selected ones of said electrodes responsive to said control means;

wherein said control means switches modes of operation responsive to said input command means to provide a stand mode, a take left step mode, a take right step mode, and a sit down mode;

wherein said electrodes are wired in pairs as channels, one adapted to contact to the right quadriceps muscle, one adapted to contact to the left quadriceps muscle, and one adapted to contact to the area of right and left peroneal nerves;

wherein during the "take right step" mode the pulse outputs are selectively outputted to the left quadriceps channel and the right peroneal channel, while at the same time no stimulus is outputted to the right quadriceps muscle and to the left peroneal nerve, said outputted to the left quadriceps channel being increased by a predefined amount during the time that no stimulus is being output to the right quadriceps channel.

6. The system as in claim 5 wherein said predefined amount is on the order of 10–20% above the immediately preceding output level.

7. The system as in claim 6 wherein said predefined amount is 15%.

8. An electrical stimulation system adapted for coupling to a patient, said system comprising:

a plurality of electrodes adapted for coupling to locations at the right and left side of a lower part of the body of a patient.

pulse generator means for selectively providing pulse generator means outputs comprising trains of pulses having selectively variable duration and pulse repetition frequency responsive to a control signal;

memory for storing operational instructions and data;

control means for selectively outputting said control signal responsive to said memory and to input commands;

pulse amplifier means for selectively amplifying pulse amplitude and power responsive to said control means and said pulse generator means;

input command means for providing mode input command signals, wherein said control means selectively provides one of a plurality of modes responsive to said input command means; and, multiplexer means for providing multiplexer means outputs responsive to selectively multiplexing outputs of said pulse amplifier means and alternatively coupling said multiplexer means output between selected ones of said electrodes responsive to said control means;

wherein said control means switches modes of operation responsive to said input command means to provide a stand mode, a take left step mode, a take right step mode, and a sit down mode;

wherein said electrodes are wired in pairs as channels, one adapted to contact to the right quadriceps muscle, one adapted to contact to the left quadriceps muscle, one adapted to contact to the right gluteus maximus muscle and one adapted to contact to the left gluteus maximus muscle;

wherein in said sit down mode the amplitude of the pulses to the right and left quadriceps channels is initially increased by a predefined amount, for a predetermined time duration, and wherein thereafter the amplitude of the pulse outputs to the right and left quadriceps channels and to the right and left gluteus maximus channels are gradually reduced to zero, over a predetermined time period on the order of seconds.

9. The systems as in claim 8 wherein said predefined amount is in the range of 10-20% above the immediately preceding amplitude levels.

10. The system as in claim 9 wherein said predefined amount is 15%.

11. The system as in claim 10 wherein said predetermined time duration is on the order of seconds.

12. An electrical stimulation system adapted for coupling to a patient, said system comprising:

a plurality of electrodes adapted for coupling to locations at the right and left side of a lower part of the body of a patient, pulse generator means for selectively providing pulse generator means outputs comprising trains of pulses having selectively variable duration and pulse repetition frequency responsive to a control signal;

memory for storing operational instructions and data;

control means for selectively outputting said control signal responsive to said memory and to input commands;

pulse amplifier means for selectively amplifying pulse amplitude and power responsive to said control means and said pulse generator means;

input command means for providing mode input command signals, wherein said control means selectively provides one of a plurality of modes responsive to said input command means; and, multiplexer means for providing multiplexer means outputs responsive to selectively multiplexing outputs of said pulse amplifier means and alternatively coupling said multiplexer means output between selected ones of said electrodes responsive to said control means;

wherein said control means switches modes of operation responsive to said input command means to provide a stand mode, a take left step mode, a take right step mode, and a sit down mode;

wherein said electrodes are wired in pairs as channels, wherein there are at least two channels one adapted to contact to the right leg quadriceps muscle and one adapted to contact to the left leg quadriceps muscle;

means for detecting a drop below a predefined threshold level in output current level of said output of said multiplexer means, and responsive to detecting said drop, to automatically activate an audible alarm, and automatically disallowing left and right step modes.

13. The system as in claim 12, said means for detecting comprises means for measuring said drop in output current level as a change in an electrical voltage drop over an impedance in parallel to the output to the stimulation electrode.

14. The system as in claim 12, said means for detecting comprises means for measuring said drop in output current level as a change in an electrical voltage drop over an impedance in series with the output to the stimulation electrodes.

15. The system as in claim 12, said means for detecting comprises means for measuring said drop in output current level as electrical impedance drop.

16. The system as in claim 8 wherein said amplitude level increase comprises an increasing peak voltage of the pulse.

17. An electrical stimulation system adapted for coupling to a patient, said system comprising:

a plurality of electrodes adapted for coupling to locations at the right and left side of a lower part of the body of a patient, pulse generator means for selectively providing pulse generator means outputs comprising trains of pulses having selectively variable duration and pulse repetition frequency responsive to a control signal;

memory for storing operational instructions and data;

control means for selectively outputting said control signal responsive to said memory and to input commands;

pulse amplifier means for selectively amplifying pulse amplitude and power responsive to said control means and said pulse generator means;

input command means for providing mode input command signals, wherein said control means selectively provides one of a plurality of modes responsive to said input command means; and, multiplexer means for providing multiplexer means outputs responsive to selectively multiplexing outputs of said pulse amplifier means and alternatively coupling said multiplexer means output between slected ones of said electrodes responsive to said control means;

wherein said control means switches modes of operation responsive to said input command means to provide a stand mode, a take left step mode, a take right step mode, and a sit down mode;

wherein said electrode are wired in pairs as channels, one adapted to contact to the right quadriceps muscle, one adapted to contact to the left quadriceps muscle, and one adapted to contact to the area of right and left peroneal nerves;

wherein during the take left step mode the pulse outputs are selectively output to the right quadriceps channel and left peroneal channel, while at the same time no stimulus is outputted to the left quadriceps muscle and to the left peroneal nerve; said output to the right quadriceps and to the left take step mode, the pulse width is increased by a predetermined amount only during that mode.

18. An electrical stimulation system adapted for coupling to a patient, said system comprising:
- a plurality of electrodes adapted for coupling to locations at the right and left side of a lower part of the body of a patient,
- pulse generator means for selectively providing pulse generator means outputs comprising trains of pulses having selectively variable duration and pulse repetition frequency responsive to a control signal;
- memory for storing operational instructions and data;
- control means for selectively outputting said control signal responsive to said memory and to input commands;
- pulse amplifier means for selectively amplifying pulse amplitude and power responsive to said control means and said pulse generator means;
- input command means for providing mode input command signals, wherein said control means selectively provides one of a plurality of modes responsive to said input command means; and,
- multiplexer means for providing multiplexer means outputs responsive to selectively multiplexing outputs of said pulse amplifier means and alternatively coupling said multiplexer means output between selected ones of said electrodes responsive to said control means;
- wherein said control means switches modes of operation responsive to said input command means to provide a stand mode, a take left step mode, a take right step mode, and a sit down mode;
- wherein said electrodes are wired in pairs as channels, one adapted to contact to the right quadriceps muscle, one adapted to contact to the left quadriceps muscle, and one adapted to contact to the area of right and left peroneal nerves;
- wherein during the take left step mode the pulse outputs are selectively output to the left quadriceps channel and the right peroneal channel, while at the same time no stimulus is outputted to the right quadriceps muscle and to the left peroneal nerve, said output to the left quadriceps channels and right peroneal nerve are modified such that during the take right step mode, the pulse width is increased by a predefined amount only during that mode.

19. An electrical stimulation system adapted for coupling to a patient, said system comprising:
- a plurality of electrodes adapted for coupling to locations at the right and left side of a lower part of the body of a patient,
- pulse generator means for selectively providing pulse generator means outputs comprising trains of pulses having selectively variable duration and pulse repetition frequency responsive to a control signal;
- memory for storing operational instructions and data;
- control means for selectively outputting said control signal responsive to said memory and to input commands;
- pulse amplifier means for selectively amplifying pulse amplitude and power responsive to said control means and said pulse generator means;
- input command means for providing mode input command signals, wherein said control means selectively provides one of a plurality of modes responsive to said input command means; and,
- multiplexer means for providing multiplexer means outputs responsive to selectively multiplexing outputs of said pulse amplifier means and alternatively coupling said multiplexer means output between selected ones of said electrodes responsive to said control means;
- wherein said control means switches modes of operation responsive to said input command means to provide a stand mode, a take left step mode, a take right step mode, and a sit down mode;
- wherein said electrodes are wired in pairs as channels, one adapted to contact to the right quadriceps muscle, one adapted to contact to the left quadriceps muscle, and one adapted to contact to the area of right and left peroneal nerves;
- wherein during the take left step mode the pulse outputs are selectively output to the right quadriceps channel and left peroneal channel, while at the same time no stimulus is outputted to the left quadriceps muscle and to the left peroneal nerve; said output to the right quadriceps and to the left take step mode, the pulse frequency is increased by a predetermined amount only during that mode.

20. An electrical stimulation system adapted for coupling to a patient, said system comprising:
- a plurality of electrodes adapted for coupling to locations at the right and left side of a lower part of the body of a patient,
- pulse generator means for selectively providing pulse generator means outputs comprising trains of pulses having selectively variable duration and pulse repetition frequency responsive to a control signal;
- memory for storing operational instructions and data;
- control means for selectively outputting said control signal responsive to said memory and to input commands;
- pulse amplifier means for selectively amplifying pulse amplitude and power responsive to said control means and said pulse generator means;
- input command means for providing mode input command signals, wherein said control means selectively provides one of a plurality of modes responsive to said input command means; and,
- multiplexer means for providing multiplexer means outputs responsive to selectively multiplexing outputs of said pulse amplifier means and alternatively coupling said multiplexer means output between selected ones of said electrodes responsive to said control means;
- wherein said control means switches modes of operation responsive to said input command means to provide a stand mode, a take left step mode, a take right step mode, and a sit down mode;
- wherein said electrodes are wired in pairs as channels, one adapted to contact to the right quadriceps muscle, one adapted to contact to the left quadriceps muscle, and one adapted to contact to the area of right and left peroneal nerves;
- wherein during the take right step mode the pulse outputs are selectively output to the left quadriceps channel and right peroneal channel, while at the same time no stimulus is outputted to the right quadriceps muscle and to the left peroneal nerve; said output to the left quadriceps channels and right peroneal nerve are modified such that during the take right step mode, the pulse frequency is increased by a predefined amount only during that mode.

21. An electrical stimulation system adapted for coupling to a patient, said system comprising:
- a plurality of electrodes adapted for coupling to locations at the right and left side of a lower part of the body of a patient,
- pulse generator means for selectively providing pulse generator means outputs comprising trains of pulses having selectively variable duration and pulse repetition frequency responsive to a control signal;
- memory for storing operational instructions and data;
- control means for selectively outputting said control signal responsive to said memory and to input commands;
- pulse amplifier means for selectively amplifying pulse amplitude and power responsive to said control means and said pulse generator means;
- input command means for providing mode input command signals, wherein said control means selectively provides one of a plurality of modes responsive to said input command means; and,
- multiplexer means for providing multiplexer means outputs responsive to selectively multiplexing outputs of said pulse amplifier means and alternatively coupling said multiplexer means output between selected ones of said electrodes responsive to said control means;
- wherein said control means switches modes of operation responsive to said input command means to provide a stand mode, a take left step mode, a take right step mode, and a sit down mode;
- wherein said electrodes are wired in pairs as channels, one adapted to contact to the right quadriceps muscle, one adapted to contact to the left quadriceps muscle, and one adapted to contact to the area of right and left peroneal nerves;
- wherein when a stimulus to the peroneal nerves at the end of a given step is ceased, then a stimulus voltage to the quadriceps of the leg taking that given step is increased in a ramp-like graduated rate versus time.

22. The system as in claim 21, where said ramp-like increase of the stimulus voltage to the quadriceps voltage lasts less than one second.

* * * * *